(12) United States Patent
Barker et al.

(10) Patent No.: US 7,562,426 B2
(45) Date of Patent: Jul. 21, 2009

(54) NEEDLING LOOPS INTO CARRIER SHEETS

(75) Inventors: James R. Barker, Francistown, NH (US); George A. Provost, Litchfield, NH (US)

(73) Assignee: Velcro Industries B.V., Curacao (AN)

( * ) Notice: Subject to any disclaimer, the term of this patent is extended or adjusted under 35 U.S.C. 154(b) by 633 days.

(21) Appl. No.: 11/102,606

(22) Filed: Apr. 8, 2005

(65) Prior Publication Data
US 2006/0225258 A1 Oct. 12, 2006

(51) Int. Cl.
*D04H 3/10* (2006.01)
(52) U.S. Cl. .......................................... 28/114; 28/161
(58) Field of Classification Search .................. 28/114, 28/107–113, 161, 159, 115, 160, 162; 156/148, 156/72; 428/85, 95, 96
See application file for complete search history.

(56) References Cited

U.S. PATENT DOCUMENTS

| | | |
|---|---|---|
| 3,348,992 A | 10/1967 | Cochran, II |
| 3,408,417 A | 10/1968 | Sogawa et al. |
| 3,535,178 A | 10/1970 | Parlin et al. |
| 3,674,618 A | 7/1972 | Spann |
| 3,704,191 A | 11/1972 | Buresh et al. |
| 3,819,462 A | 6/1974 | Starr et al. |
| 3,950,587 A | 4/1976 | Colijn et al. |
| 4,001,472 A | 1/1977 | Thomas et al. |
| 4,035,533 A | 7/1977 | Chambley |
| 4,116,892 A | 9/1978 | Schwarz |
| 4,131,704 A | 12/1978 | Erickson et al. |
| 4,154,889 A | 5/1979 | Platt |
| 4,192,086 A | 3/1980 | Sichak |
| 4,223,059 A | 9/1980 | Schwarz |
| 4,258,094 A | 3/1981 | Benedyk |
| 4,258,097 A | 3/1981 | Benedyk |

(Continued)

FOREIGN PATENT DOCUMENTS

DE 101 39 842 A1 4/2003

(Continued)

OTHER PUBLICATIONS

Dilo Group, "Market Leadership in Nonwovens Technology", Pakistan Textile Journal, date unknown (2 pages).

(Continued)

*Primary Examiner*—Amy B Vanatta
(74) *Attorney, Agent, or Firm*—Fish & Richardson P.C.

(57) ABSTRACT

Methods of forming a loop product are provided. Some methods include (a) introducing a sheet-form substrate and a layer of polymeric fibers into a needle loom, with the fibers disposed on a first surface of the substrate, and (b) needling the fibers through the substrate to form hook-engageable loop structures of the fibers extending from a second surface of the substrate through holes formed in the substrate by the needling. Needling the fibers includes piercing the substrate with a plurality of needles while advancing the substrate in a machine direction at a predetermined speed, while cyclically advancing the needles in the machine direction, during piercing of the substrate, in a manner that causes the needles to travel in a substantially elliptical path, such that while the needles extend through the substrate the needles are moving in the machine direction.

25 Claims, 8 Drawing Sheets

U.S. PATENT DOCUMENTS

| | | | |
|---|---|---|---|
| 4,295,251 A | 10/1981 | Tatham et al. | |
| 4,320,167 A | 3/1982 | Wishman | |
| 4,342,802 A | 8/1982 | Pickens, Jr. et al. | |
| 4,377,889 A | 3/1983 | Tatham et al. | |
| 4,379,189 A | 4/1983 | Platt | |
| 4,389,442 A | 6/1983 | Pickens, Jr. et al. | |
| 4,389,443 A | 6/1983 | Thomas et al. | |
| 4,391,866 A | 7/1983 | Pickens, Jr. et al. | |
| 4,418,104 A | 11/1983 | Kiyomura et al. | |
| 4,446,189 A | 5/1984 | Romanek | |
| 4,451,314 A | 5/1984 | Knoke et al. | |
| 4,490,425 A | 12/1984 | Knoke et al. | |
| 4,521,472 A | 6/1985 | Gold | |
| 4,536,439 A | 8/1985 | Forsten | |
| 4,600,605 A | 7/1986 | Nakai et al. | |
| 4,600,618 A | 7/1986 | Raychok, Jr. et al. | |
| 4,609,581 A | 9/1986 | Ott | |
| 4,645,699 A | 2/1987 | Neveu | |
| 4,654,246 A | 3/1987 | Provost et al. | |
| 4,750,443 A | 6/1988 | Blaustein et al. | |
| 4,770,917 A | 9/1988 | Tochacek et al. | |
| 4,931,343 A | 6/1990 | Becker et al. | |
| 5,032,122 A | 7/1991 | Noel et al. | |
| 5,080,951 A | 1/1992 | Guthrie | 428/85 |
| 5,144,730 A | 9/1992 | Dilo | |
| 5,216,790 A | 6/1993 | Eschenbach | |
| 5,254,194 A | 10/1993 | Ott et al. | |
| 5,256,231 A | 10/1993 | Gorman et al. | |
| 5,326,612 A | 7/1994 | Goulait | |
| 5,380,580 A | 1/1995 | Rogers et al. | |
| 5,391,424 A | 2/1995 | Kolzer | |
| 5,407,439 A | 4/1995 | Goulait | |
| 5,407,722 A | 4/1995 | Peake, III et al. | |
| 5,447,590 A | 9/1995 | Gilpatrick | |
| 5,449,530 A | 9/1995 | Peake, III et al. | |
| 5,470,417 A | 11/1995 | Goulait | |
| 5,500,268 A | 3/1996 | Billarant | |
| 5,518,795 A | 5/1996 | Kennedy et al. | |
| 5,547,531 A | 8/1996 | Allen et al. | |
| 5,571,097 A | 11/1996 | Seth | |
| 5,599,601 A | 2/1997 | Polski et al. | |
| 5,603,708 A | 2/1997 | Seth | |
| 5,605,729 A | 2/1997 | Mody et al. | |
| 5,611,789 A | 3/1997 | Seth | |
| 5,611,791 A | 3/1997 | Gorman et al. | |
| 5,614,232 A | 3/1997 | Torigoe et al. | |
| 5,614,281 A | 3/1997 | Jackson et al. | |
| 5,615,460 A | 4/1997 | Weirich et al. | |
| 5,616,155 A | 4/1997 | Kronzer | |
| 5,616,394 A | 4/1997 | Gorman et al. | |
| 5,622,578 A | 4/1997 | Thomas | |
| 5,630,896 A | 5/1997 | Corbin et al. | |
| 5,643,397 A | 7/1997 | Gorman et al. | |
| 5,654,070 A | 8/1997 | Billarant | |
| 5,660,911 A | 8/1997 | Tesch | |
| 5,669,900 A | 9/1997 | Bullwinkel et al. | |
| 5,685,756 A | 11/1997 | Noda | |
| 5,692,949 A | 12/1997 | Sheffield et al. | |
| 5,707,707 A | 1/1998 | Burnes et al. | |
| 5,707,906 A | 1/1998 | Eschenbach | |
| 5,732,453 A * | 3/1998 | Dilo et al. | 28/114 |
| 5,759,926 A | 6/1998 | Pike et al. | |
| 5,763,041 A | 6/1998 | Leak et al. | |
| 5,773,120 A | 6/1998 | Deka et al. | |
| 5,786,060 A | 7/1998 | Takahashi et al. | |
| 5,814,390 A | 9/1998 | Stokes et al. | |
| 5,843,057 A | 12/1998 | McCormack | |
| 5,858,515 A | 1/1999 | Stokes et al. | |
| 5,866,222 A | 2/1999 | Seth et al. | |
| 5,888,607 A | 3/1999 | Seth et al. | |
| 5,891,547 A | 4/1999 | Lawless | |
| 5,904,793 A | 5/1999 | Gorman et al. | |
| 5,931,823 A | 8/1999 | Stokes et al. | |
| 5,945,215 A | 8/1999 | Bersted et al. | |
| 5,962,102 A | 10/1999 | Sheffield et al. | |
| 5,962,112 A | 10/1999 | Haynes et al. | |
| 5,964,742 A | 10/1999 | McCormack et al. | |
| 5,997,981 A | 12/1999 | McCormack et al. | |
| 6,051,094 A | 4/2000 | Melbye et al. | |
| 6,086,984 A | 7/2000 | DiMaggio, Jr. et al. | |
| 6,093,665 A | 7/2000 | Sayovitz et al. | |
| 6,129,879 A | 10/2000 | Bersted et al. | |
| 6,129,964 A | 10/2000 | Seth | |
| 6,158,097 A * | 12/2000 | Dilo | 28/114 |
| 6,161,269 A | 12/2000 | Dilo et al. | |
| 6,162,522 A | 12/2000 | Deka et al. | |
| 6,192,556 B1 | 2/2001 | Kikko et al. | |
| 6,195,850 B1 | 3/2001 | Melbye et al. | |
| 6,265,053 B1 | 7/2001 | Kronzer et al. | |
| 6,329,016 B1 | 12/2001 | Shepard et al. | |
| 6,342,285 B1 | 1/2002 | Shepard et al. | |
| 6,355,759 B1 | 3/2002 | Sherman et al. | |
| 6,368,444 B1 | 4/2002 | Jameson et al. | |
| 6,410,138 B2 | 6/2002 | Mleziva et al. | |
| 6,454,989 B1 | 9/2002 | Neely et al. | |
| 6,489,004 B1 | 12/2002 | Martin et al. | |
| 6,537,935 B1 | 3/2003 | Seth et al. | |
| 6,598,276 B2 | 7/2003 | Shepard et al. | |
| 6,638,611 B2 | 10/2003 | Seth | |
| 6,642,160 B1 | 11/2003 | Takahashi | |
| 6,642,429 B1 | 11/2003 | Carter et al. | |
| 6,645,611 B2 | 11/2003 | Seth | |
| 6,660,202 B2 | 12/2003 | Shepard et al. | |
| 6,686,303 B1 | 2/2004 | Haynes et al. | |
| 6,703,086 B2 | 3/2004 | Kronzer et al. | |
| 6,709,996 B2 | 3/2004 | Mleziva et al. | |
| 6,716,511 B2 | 4/2004 | Bersted et al. | |
| 6,740,385 B2 | 5/2004 | Gardner et al. | |
| 6,756,327 B2 | 6/2004 | Martin | |
| 6,783,834 B2 | 8/2004 | Shepard et al. | |
| 6,849,142 B1 | 2/2005 | Goulait | |
| 6,869,659 B2 | 3/2005 | Shepard et al. | |
| 6,948,221 B2 * | 9/2005 | Fuchs | 28/107 |
| 7,117,571 B2 * | 10/2006 | Dilo | 28/107 |
| 7,276,642 B2 | 10/2007 | Belau | |
| 7,282,251 B2 | 10/2007 | Provost et al. | |
| 2004/0020579 A1 | 2/2004 | Durrance et al. | |
| 2004/0072491 A1 | 4/2004 | Gillette et al. | |
| 2004/0131820 A1 | 7/2004 | Turner | |
| 2004/0157036 A1 | 8/2004 | Provost et al. | |
| 2005/0196580 A1 | 9/2005 | Provost et al. | |
| 2005/0196581 A1 | 9/2005 | Provost et al. | |
| 2005/0196583 A1 | 9/2005 | Provost et al. | |
| 2005/0208259 A1 | 9/2005 | Provost et al. | |
| 2005/0217092 A1 | 10/2005 | Barker et al. | |
| 2006/0105664 A1 | 5/2006 | Zafiroglu | |
| 2006/0183389 A1 | 8/2006 | Zafiroglu | |
| 2007/0178273 A1 | 8/2007 | Provost et al. | |
| 2008/0113152 A1 | 5/2008 | Provost et al. | |

FOREIGN PATENT DOCUMENTS

| | | |
|---|---|---|
| EP | 0 211 564 | 2/1992 |
| EP | 0 482 749 A1 | 4/1992 |
| EP | 0 325 473 | 3/1993 |
| EP | 0 765 616 A1 | 4/1997 |
| EP | 0 780 505 A2 | 6/1997 |
| EP | 0 598 085 | 7/1997 |
| EP | 0 597 075 | 4/1998 |
| EP | 0 937 420 | 8/1999 |
| EP | 0 726 977 | 6/2000 |
| EP | 1 132 511 | 9/2001 |
| EP | 0 861 137 | 1/2002 |
| EP | 1 279 348 | 1/2003 |

| | | |
|---|---|---|
| EP | 1 279 348 A1 | 1/2003 |
| EP | 1 156 767 | 10/2004 |
| EP | 1 113 099 | 3/2006 |
| JP | 6-33359 | 2/1994 |
| JP | 06-123061 | 5/1994 |
| JP | 7-171011 | 7/1995 |
| JP | 08-27657 | 1/1996 |
| JP | 09-195155 | 7/1997 |
| JP | 10-146207 | 6/1998 |
| JP | 10-151005 | 6/1998 |
| JP | 2971332 | 11/1999 |
| JP | 2001-212 | 1/2001 |
| JP | 2001-8713 | 1/2001 |
| JP | 3134709 | 2/2001 |
| JP | 2001-207369 | 8/2001 |
| JP | 2001-514346 | 9/2001 |
| JP | 2002-10807 | 1/2002 |
| JP | 2003-265207 | 9/2003 |
| JP | 2004-194730 | 7/2004 |
| JP | 3855084 | 12/2006 |
| JP | 3877842 | 2/2007 |
| WO | WO98/33410 | 8/1998 |
| WO | WO99/11452 | 3/1999 |
| WO | WO01/80680 | 1/2001 |
| WO | WO03/051251 | 6/2003 |
| WO | WO2004/019305 | 3/2004 |
| WO | WO2004/049853 | 6/2004 |
| WO | WO2004/058497 | 7/2004 |
| WO | WO2004/059061 | 7/2004 |
| WO | WO2004/058118 | 7/2005 |
| WO | WO2004/059117 | 7/2005 |

OTHER PUBLICATIONS

Dilo, "Engineering Excellence in Needle Looms!", Hyperpunch—The Solution for Fine and Quality Fleeces, Synthetic Leather, Spunbondeds, Papermachine Felts!, date unknown (2 pages).
Purdy, Terry, Dilo Inc., Needle Punching Benefits from Elliptical Needle Paths, date unknown (13 pages).
U.S. Appl. No. 12/133,769, filed Jun. 5, 2008, Barker et al.
U.S. Appl. No. 12/133,945, filed Jun. 5, 2008, Provost et al.

* cited by examiner

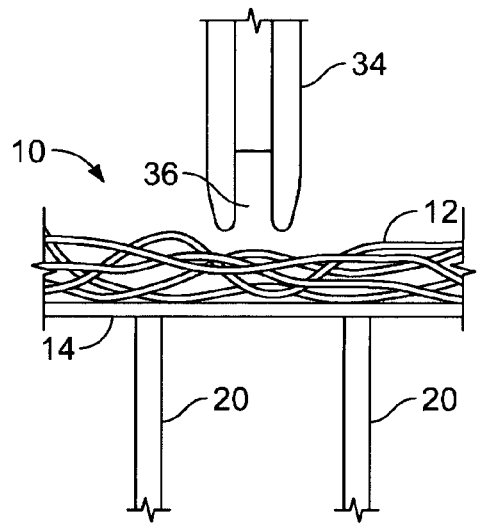
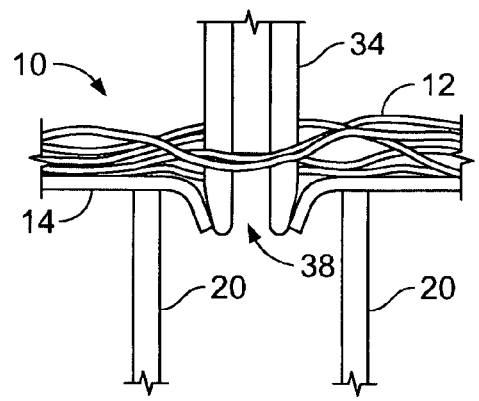
FIG. 2A  FIG. 2B
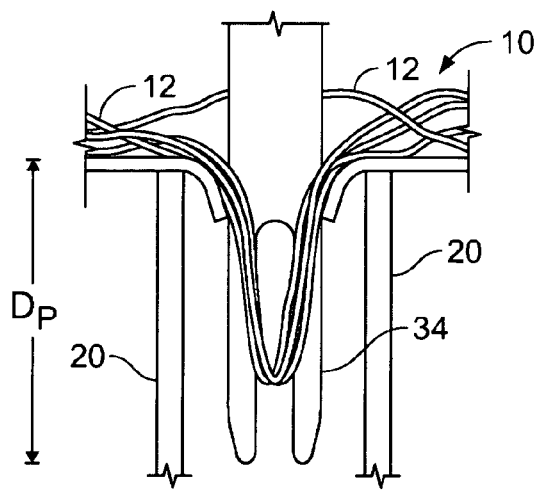
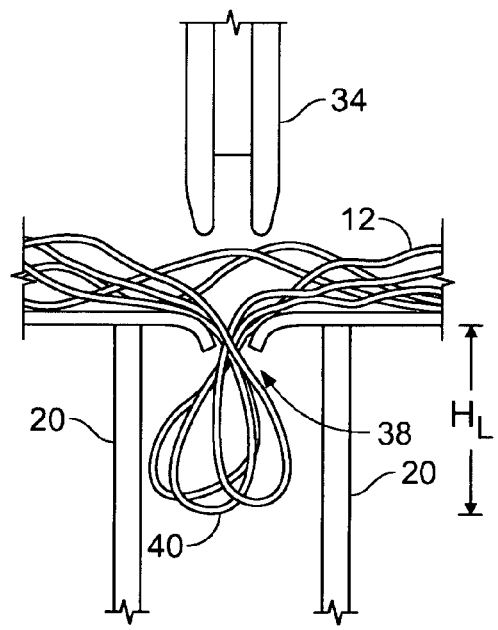
FIG. 2C  FIG. 2D

NEEDLING LOOPS INTO CARRIER SHEETS

TECHNICAL FIELD

This invention relates to methods of making products having loops, such as for hook-and-loop fastening, and products produced by such methods.

BACKGROUND

Touch fasteners are particularly desirable as fastening systems for lightweight, disposable garments, such as diapers. In an effort to provide a cost-effective loop material, some have recommended various alternatives to weaving or knitting, such as by needling a lightweight layer of fibers to form a light non-woven material that can then be stretched to achieve even lighter basis weight and cost efficiency, with the loop structures anchored by various binding methods, and subsequently adhered to a substrate. U.S. Pat. No. 6,329,016 teaches one such method, for example.

Inexpensive loop materials are desired, for touch fastening and other purposes, with particular characteristics suitable for various applications.

SUMMARY

In one aspect of the invention, a method of forming a loop product includes: introducing a sheet-form substrate and a layer of polymeric fibers into a needle loom, with the fibers disposed on a first surface of the substrate; and needling the fibers through the substrate to form hook-engageable loop structures of the fibers extending from a second surface of the substrate through holes formed in the substrate by the needling. Needling the fibers includes: piercing the substrate with a plurality of needles while advancing the substrate in a machine direction at a predetermined speed, while cyclically advancing the needles in the machine direction, during piercing of the substrate, in a manner that causes the needles to travel in a substantially elliptical path, such that while the needles extend through the substrate the needles are moving in the machine direction.

In some embodiments, the method also includes anchoring the loop structures to resist fiber pullout under fastening loads after needling. In some cases, anchoring includes laminating fiber portions to the first surface of the substrate. In some of these cases, laminating includes passing the needled substrate through a nip between two rolls (e.g. a nip wherein one roll of the nip is covered with a card cloth), one of the two rolls having a plurality of pins extending from its surface. In some instances, the method also includes preheating (e.g. using infrared energy) the needled substrate prior to delivering it to the nip. In some of these cases, laminating is performed in a manner so as to avoid crushing the loop structures. In some cases, the method also includes embossing the loop product after anchoring the loop structures.

In some embodiments, the fibers include bicomponent fibers that include an inner layer and an outer layer, the outer layer having a lower softening temperature than the inner layer. In some cases, anchoring includes heating the needled substrate sufficiently to soften the outer layer of the bicomponent fibers and fuse fiber portions to the first surface of the substrate. In some cases, the bicomponent fibers comprise core-sheath fibers wherein the sheath has a lower melting point than the core. Examples include embodiments where the core is a polyester and the sheath is a copolyester and embodiments where the sheath is formed of a polymer having a melting temperature of about 110 degrees C. In some cases, the fibers comprise a blend of bicomponent fibers and single component fibers (e.g. between about 15 and 30 percent bicomponent fibers, by weight).

In some embodiments, the needling step also includes providing a bed of brushes or lamella into which the needles penetrate after piercing the substrate.

In some embodiments, the predetermined speed of the substrate is at least 30 meters per minute. In some cases, the needling step includes a random velouring process.

In some embodiments, the holes are substantially round. In some other embodiments, the holes are oval and have a length, in the machine direction, which is less than 20 percent greater than their width in a cross-machine direction.

In some embodiments, the substrate includes a polymer film. In some embodiments, the substrate includes a scrim. In some embodiments, the substrate includes paper.

In some embodiments, the needling step includes elliptical needling. In some embodiments, the needling step include needling into a moving support (e.g. a brush apron).

In another aspect of the invention, a needling loom includes: an array of needles; a bed of bristles configured to support a sheet form substrate and carry the substrate past the array of needles in a machine direction, and a drive mechanism configured to move the array of needles in a cyclic motion to repetitively needle the moving substrate; wherein the cyclic motion of the needles moves the needles in the machine direction while the needles extend through the substrate.

The phrase "random velouring," as used herein, refers to needling fibers, from only one direction, into a substrate supported on something other than a bed plate with holes. The support may be, for example, a bristle bed, a flat lammela bed, or a stack of lammela disks.

In some implementations, loop materials are provided that are lightweight and low cost, and yet can withstand particularly high shear and peel loads, especially when combined with appropriately sized male fastener elements. In some cases, the tensile strength of the base of the fastener product is derived at least in part from the carrier sheet (or, in cases where the binder is a sheet product, from the binder sheet), and thus there need only be sufficient fibers to generate the anchored loop structures, enabling a reduction in requirements for high-tenacity fiber. The binder can be selected of a material not necessarily weld-compatible with the fiber material, as the loop structures can be anchored by fusing the binder directly to the carrier sheet to encapsulate portions of the fibers and mechanically anchor the bases of the loop structures. This can enable the use of fiber materials preferred for their fastening performance, with binders selected for compatibility with a substrate in a given application.

The invention can provide loop materials containing surprisingly low basis weights of fiber, and low overall weight and thickness, particularly suitable for low-cycle, disposable products and applications.

The use of powdered, or otherwise loose particulate-form binders can reduce the overall weight of binder needed to secure the loop structures, as the binder can penetrate between the fibers and into base regions of the loop structures near the holes of the carrier sheet prior to fusing. Vibration of the powdered fibers prior to fusing can enhance this penetration.

The invention can provide a cost-effective means for providing engageable loops on an otherwise loop-free carrier sheet, by selective needling. Such carrier sheets can then be processed into substrates for given applications, such as into outer membranes of disposable diapers. This can eliminate a step of bonding a loop material to the substrate in the production of such products, the partially loop-carrying material becoming the substrate.

The invention can, in various aspects, also provide a cost-effective stretchable loop product.

The details of one or more embodiments of the invention are set forth in the accompanying drawings and the description below. Other features and advantages of the invention will be apparent from the description and drawings, and from the claims.

DESCRIPTION OF DRAWINGS

FIGS. 2A-2D are diagrammatic side views of stages of a needling step of the process of FIG. 1.

Like reference symbols in the various drawings indicate like elements.

DETAILED DESCRIPTION

Descriptions of loop products will follow a description of some methods of making loop products.

Figure 1:
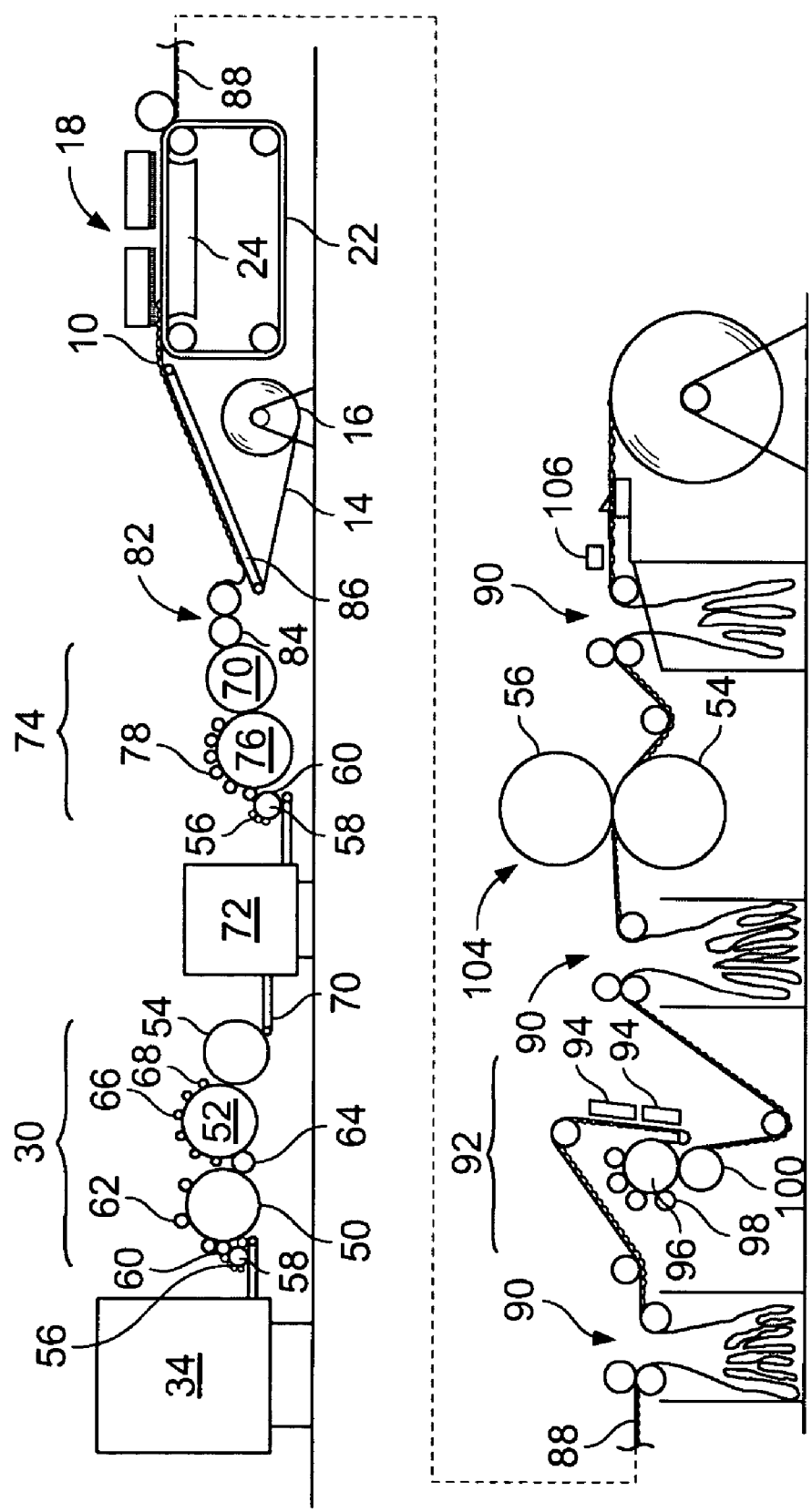
FIG. 1 is a diagrammatic view of a process for forming loop material.

FIG. 1 illustrates a machine and process for producing an inexpensive touch fastener loop product. Beginning at the upper left end of FIG. 1, a carded and cross-lapped layer of fibers 10 is created by two carding stages with intermediate cross-lapping. Weighed portions of staple fibers of different types are fed to the first carding station 30 by a card feeder 34. Card station 30 includes a 36-inch breast roll 50, a 60-inch breaker main 52, and a 50-inch breaker doffer 54. The first card feedroll drive includes 3-inch feedrolls 56 and a 3-inch cleaning roll on a 13-inch lickerin roll 58. An 8-inch angle stripper 60 transfers the fiber to breast roll 50. There are three 8-inch worker roll sets 62 on the breast roll, and a 16-inch breast doffer 64 feeds breaker main 52, against which seven 8-inch worker sets 66 and a flycatcher 68 run. The carded fibers are combed onto a conveyer 70 that transfers the single fiber layer into a cross-lapper 72. Before cross-lapping, the carded fibers still appear in bands or streaks of single fiber types, corresponding to the fibrous balls fed to carding station 30 from the different feed bins. Cross-lapping, which normally involves a 90-degree reorientation of line direction, overlaps the fiber layer upon itself and is adjustable to establish the width of fiber layer fed into the second carding station 74. In this example, the cross-lapper output width is set to approximately equal the width of the carrier into which the fibers will be needled. Cross-lapper 72 may have a lapper apron that traverses a floor apron in a reciprocating motion. The cross-lapper lays carded webs of, for example, about 80 inches (1.5 meters) width and about one-half inch (1.3 centimeters) thickness on the floor apron, to build up several layers of criss-crossed web to form a layer of, for instance, about 80 inches (1.5 meters) in width and about 4 inches (10 centimeters) in thickness, comprising four double layers of carded web. During carding, the fibers are separated and combed into a cloth-like mat consisting primarily of parallel fibers. With nearly all of its fibers extending in the carding direction, the mat has some strength when pulled in the carding direction but almost no strength when pulled in the carding cross direction, as cross direction strength results only from a few entanglements between fibers. During cross-lapping, the carded fiber mat is laid in an overlapping zigzag pattern, creating a mat 10 of multiple layers of alternating diagonal fibers. The diagonal layers, which extend in the carding cross direction, extend more across the apron than they extend along its length.

Cross-lapping the web before the second carding process provides several tangible benefits. For example, it enhances the blending of the fiber composition during the second carding stage. It also allows for relatively easy adjustment of web width and basis weight, simply by changing cross-lapping parameters.

Second carding station 74 takes the cross-lapped mat of fibers and cards them a second time. The feedroll drive consists of two 3-inch feed rolls and a 3-inch cleaning roll on a 13-inch lickerin 58, feeding a 60-inch main roll 76 through an 8-inch angle stripper 60. The fibers are worked by six 8-inch worker rolls 78, the last five of which are paired with 3-inch strippers. A 50-inch finisher doffer 80 transfers the carded web to a condenser 82 having two 8-inch condenser rolls 84, from which the web is combed onto a carrier sheet 14 fed from spool 16. The condenser increases the basis weight of the web from about 0.7 osy (ounce per square yard) to about 1.0 osy, and reduces the orientation of the fibers to remove directionality in the strength or other properties of the finished product.

The carrier sheet 14, such as polymer film or paper, may be supplied as a single continuous length, or as multiple, parallel strips. For particularly wide webs, it may be necessary or cost effective to introduce two or more parallel sheets, either adjacent or slightly overlapping. The parallel sheets may be unconnected or joined along a mutual edge. The carded, uniformly blended layer of fibers from condenser 82 is carried up conveyor 86 on carrier sheet 14 and into needling station 18. As the fiber layer enters the needling station, it has no stability other than what may have been imparted by carding and cross-lapping. In other words, the fibers are not pre-needled or felted prior to needling into the carrier sheet. In this state, the fiber layer is not suitable for spooling or accumulating prior to entering the needling station.

In needling station 18, the carrier sheet 14 and fiber are needle-punched from the fiber side. The needles are guided through a stripping plate above the fibers, and draw fibers through the carrier sheet 14 to form loops on the opposite side. During needling, the carrier sheet is supported on a bed of pins or bristles extending from a driven support belt or brush apron 22 that moves with the carrier sheet through the needling station. Alternatively, carrier sheet 14 can be supported on a screen or by a standard stitching plate (not shown). Reaction pressure during needling is provided by a stationary reaction plate 24 underlying apron 22. In this example, needling station 18 needles the fiber-covered carrier sheet 14 with an overall penetration density of about 80 to 160 punches per square centimeter. At this needling density and with a carrier sheet of a polypropylene film of a thickness of about 0.0005 inch (0.013 millimeter), we have found that 38 gauge forked tufting needles were small enough to not obliterate the film, leaving sufficient film interconnectivity that the film continued to exhibit some dimensional stability within its plane. With the same parameters, larger 30 gauge needles essentially segmented the film into small, discrete pieces entangled within the fibers. During needling, the thickness of the carded fiber layer only decreases by about half, as compared with felting processes in which the fiber layer thickness decreases by one or more orders of magnitude. As fiber basis weight decreases, needling density may need to be increased.

The needling station 18 may be a "structuring loom" configured to subject the fibers and carrier web to a random velouring process. Thus, the needles penetrate a moving bed of bristles arranged in an array (brush apron 22). The brush apron may have a bristle density of about 2000 to 3000 bristles per square inch (310 to 465 bristles per square centimeter), e.g., about 2570 bristles per square inch (400 per square centimeter). The bristles are each about 0.018 inch (0.46 millimeter) in diameter and about 20 millimeters long, and are preferably straight. The bristles may be formed of any suitable material, for example 6/12 nylon. Suitable brushes may be purchased from Stratosphere, Inc., a division of Howard Brush Co., and retrofitted onto DILO and other random velouring looms. Generally, the brush apron moves at the desired line speed.

Alternatively, other types of structuring looms may be used, for example those in which the needles penetrate into a plurality of lamella or lamellar disks.

FIGS. 2A through 2D sequentially illustrate the formation of a loop structure by needling. As a forked needle enters the fiber mat 10 (FIG. 2A), some individual fibers 12 will be captured in the cavity 36 in the forked end of the needle. As needle 34 pierces film 14 (FIG. 2B), these captured fibers 12 are drawn with the needle through the hole 38 formed in the film to the other side of the film. As shown, film 14 remains generally supported by pins 20 through this process, the penetrating needle 34 entering a space between adjacent pins. Alternatively, film 14 can be supported by a screen or stitching plate (not shown) that defines holes aligned with the needles. As needle 34 continues to penetrate (FIG. 2C), tension is applied to the captured fibers, drawing mat 10 down against film 14. In this example, a total penetration depth "$D_p$" of about 5.0 millimeters, as measured from the entry surface of film 14, was found to provide a well-formed loop structure without overly stretching fibers in the remaining mat. Excessive penetration depth can draw loop-forming fibers from earlier-formed tufts, resulting in a less robust loop field. Penetration depths of 2 and 7 millimeters also worked in this example, although the 5.0 millimeter penetration is presently preferred. When needle 34 is retracted (FIG. 2D), the portions of the captured fibers 12 carried to the opposite side of the carrier web remain in the form of a plurality of individual loops 40 extending from a common trunk 42 trapped in film hole 38. As shown, residual stresses in the film 14 around the hole, acting to try to restore the film to its planar state, can apply a slight pressure to the fibers in the hole, helping to secure the base of the loop structure. The film can also help to resist tension applied to the fiber remaining on the mat side of the film that would tend to pull the loops back through the hole. The final loop formation preferably has an overall height "$H_L$" of about 0.040 to 0.090 inch (1.0 to 2.3 millimeters), for engagement with the size of male fastener elements commonly employed on disposable garments and such.

Advance per stroke is limited due to a number of constraints, including needle deflection and potential needle breakage. Thus, it may be difficult to accommodate increases in line speed and obtain an economical throughput by adjusting the advance per stroke. As a result, the holes pierced by the needles may become elongated, due to the travel of the carrier sheet while the needle is interacting with the carrier sheet (the "dwell time"). This elongation is generally undesirable, as it reduces the amount of support provided to the base of each of the loop structures by the surrounding substrate, and may adversely affect resistance to loop pull-out. Moreover, this elongation will tend to reduce the mechanical integrity of the carrier film due to excessive drafting, i.e., stretching of the film in the machine direction and corresponding shrinkage in the cross-machine direction.

Figure 2E:
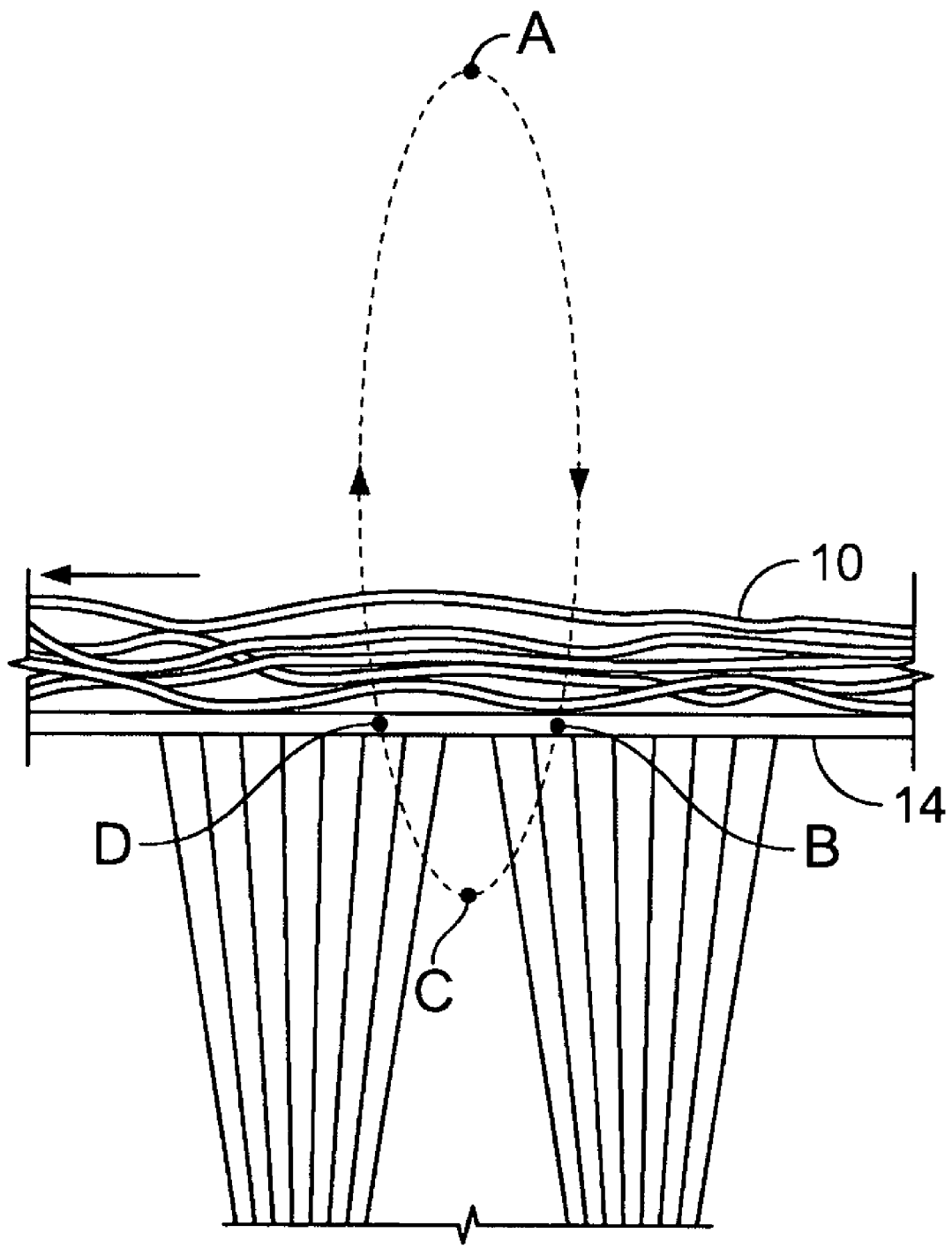
FIG. 2E is a diagrammatic side view showing an elliptical path that may be followed by the needle during needling.

Elongation of the holes may be reduced or eliminated by causing the needles to travel in a generally elliptical path, viewed from the side. This elliptical path is shown schematically in FIG. 2E. Referring to FIG. 2E, each needle begins at a top "dead" position A, travels downward to pierce the film (position B) and, while it remains in the film (from position B through bottom "dead" position C to position D), moves forward in the machine direction. When the needle has traveled upward sufficiently for its tip to have exited the pierced opening (position D), it continues to travel upward, free of the film, while also returning horizontally (opposite to the machine direction) to its normal, rest position (position A), completing the elliptical path. This elliptical path of the needles is accomplished by moving the entire needle board simultaneously in both the horizontal and vertical directions. Needling in this manner is referred to herein as "elliptical needling." Needling looms that perform this function are available from DILO System Group, Eberbach, Germany, under the tradename "HYPERPUNCH Systems."

During elliptical needling, the horizontal travel of the needle board is preferably roughly equivalent to the distance that the film advances during the dwell time. The horizontal travel is a function of needle penetration depth, vertical stroke length, carrier film thickness, and advance per stroke. Generally, at a given value of needle penetration and film thickness, horizontal stroke increases with increasing advance per stroke. At a fixed advance per stroke, the horizontal stroke generally increases as depth of penetration and web thickness increases.

For example, for a polypropylene film having a thickness of 0.0005 inch (so thin that it is not taken into account), a loom outfeed of 18.9 m/min, an effective needle density of 15,006 needles/meter, a vertical stroke of 35 mm, a needle penetration of 5.0 mm, and a headspeed of 2,010 strokes/min, the preferred horizontal throw (i.e., the distance between points B and D in FIG. 2E) would be 3.3 mm, resulting in an advance per stroke of 9.4 mm.

Using elliptical needling, it may be possible to obtain line speeds 30 ypm (yards/minute) or mpm (meters/minute) or greater, e.g., 50 ypm or mpm, for example 60 ypm. Such speeds may be obtained with minimal elongation of the holes, for example the length of the holes in the machine direction may be less than 20% greater than the width of the holes in the cross-machine direction, preferably less than 10% greater and in some instances less than 5% greater.

For needling longitudinally discontinuous regions of the material, such as to create discrete loop regions as discussed further below, the needle boards can be populated with needles only in discrete regions, and the needling action paused while the material is indexed through the loom between adjacent loop regions. Effective pausing of the needling action can be accomplished by altering the penetration depth of the needles during needling, including to needling depths at which the needles do not penetrate the carrier sheet. Such needle looms are available from FEHRER AG in Austria, for example. Alternatively, means can be implemented to selectively activate smaller banks of needles within the loom according to a control sequence that causes the banks to be activated only when and where loop structures are desired. Lanes of loops can be formed by a needle loom with lanes of needles separated by wide, needle-free lanes.

In the example illustrated, the needled product 88 leaves needling station 18 and brush apron 22 in an unbonded state, and proceeds to a lamination station 92. If the needling step was performed with the carrier sheet supported on a bed of rigid pins, lamination can be performed with the carrier sheet still carried on the bed of pins. Prior to the lamination station, the web passes over a gamma gage (not shown) that provides a rough measure of the mass per unit area of the web. This measurement can be used as feedback to control the upstream carding and cross-lapping operations. The web is stable enough at this stage to be accumulated in an accumulator 90 between the needling and lamination stations. As known in the art, accumulator 90 is followed by a spreading roll (not shown) that spreads and centers the web prior to entering the next process. Prior to lamination, the web may also pass through a coating station (not shown) in which a binder is applied to enhance lamination. In lamination station 92, the web first passes by one or more infrared heaters 94 that preheat the fibers and/or carrier sheet from the side opposite the loops. In products relying on bicomponent fibers for bonding, heaters 94 preheat and soften the sheaths of the bicomponent fibers. In one example, the heater length and line speed are such that the web spends about four seconds in front of the heaters. Just downstream of the heaters is a web temperature sensor (not shown) that provides feedback to the heater control to maintain a desired web exit temperature. For lamination, the heated web is trained about a hot can 96 against which four idler card cloth-covered rolls 98 of five inch (13 centimeters) solid diameter (excluding the card cloth), and a driven, rubber, card cloth-covered roll 100 of 18 inch (46 centimeters) solid diameter, rotate under controlled pressure. The pins of the card cloth rolls 98,100 thus press the web against the surface of hot can 96 at discrete pressure points, thus bonding the fibers at discrete locations without crushing other fibers, generally between the bond points, that remain exposed and open for engagement by hooks. For many materials, the bonding pressure between the card cloth rolls and the hot can is quite low, in the range of 1-10 pounds per square inch (70-700 grams per square centimeter) or less. The surface of hot can 96 is maintained at a temperature of about 306 degrees Fahrenheit (150 degrees Celsius) for one example employing bicomponent polyester fiber and polypropylene film, to just avoid melting the polypropylene film. The hot can 96 can have a compliant outer surface, or be in the form of a belt. As an alternative to roller nips, a flatbed fabric laminator (not shown) can be employed to apply a controlled lamination pressure for a considerable dwell time. Such flatbed laminators are available from Glenro Inc. in Paterson, N.J. In some applications, the finished loop product is passed through a cooler (not shown) prior to embossing.

The pins extending from card cloth-covered rolls 98,100 are arranged in an array of rows and columns, with a pin density of about 200 and 350 pins per square inch (31 to 54 pins per square centimeter) in a flat state, preferred to be between about 250 to 300 pins per square inch (39 to 47 pins per square centimeter). The pins are each about 0.020 inch (0.5 millimeter) in diameter, and are preferably straight to withstand the pressure required to laminate the web. The pins extend from a backing about 0.25 inch (6.4 millimeters) in thickness. The backing is of two layers of about equal thickness, the lower layer being of fibrous webbing and the upper layer being of rubber. The pins extend about 0.25 inch (6.4 millimeters) from the rubber side of the backing. Because of the curvature of the card cloth rolls, the effective density of the pin tips, where lamination occurs, is lower than that of the pins with the card cloth in a flat state. A flat state pin density of 200 to 350 pins per square inch (31 to 54 pins per square centimeter) equates to an effective pin density of only 22 to 38 pins per square centimeter on idler rolls 98, and 28 to 49 pins per square centimeter on driven rubber roll 100. In most cases, it is preferable that the pins not penetrate the carrier sheet during bonding, but that each pin provide sufficient support to form a robust bond point between the fibers. In a non-continuous production method, such as for preparing discrete patches of loop material, a piece of carrier sheet 14 and a section of fiber mat 12 may be layered upon a single card cloth, such as are employed for carding webs, for needling and subsequent bonding, prior to removal from the card cloth.

Figure 3:
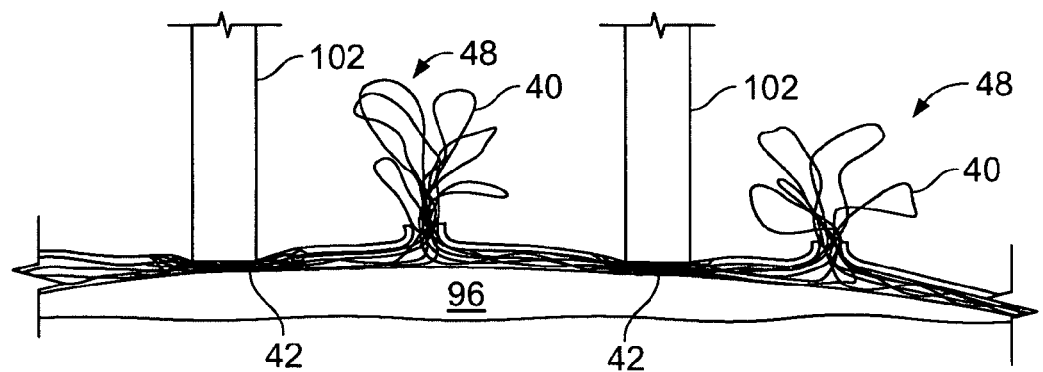
FIG. 3 is an enlarged diagrammatic view of a lamination nip through which the loop material passes during the process of FIG. 1.

FIG. 3 is an enlarged view of the nip between hot can 96 and one of the card cloth rolls. As discussed above, due to the curvature of the card cloth rolls, their pins 102 splay outward, such that the effective pin density at the hot can is lower than that of the card cloth in a planar state. The pins contact the carrier sheet (or its remnants, depending on needling density) and fuse underlying fibers to each other and/or to material of the carrier sheet, forming a rather solid mass 42 of fused material in the vicinity of the pin tip, and a penumbral area of fused but distinct fibers surrounding each pin. The laminating parameters can be varied to cause these penumbral, partially fused areas to be overlapped if desired, creating a very strong, dimensionally stable web of fused fibers across the non-working side of the loop product that is still sufficiently flexible for many uses. Alternatively, the web can be laminated such that the penumbral areas are distinct and separate, creating a looser web. For most applications the fibers should not be continuously fused into a solid mass across the back of the product, in order to retain a good hand and working flexibility. The number of discrete fused areas per unit area of the bonded web is such that staple fibers with portions extending through holes to form engageable loops 40 that have other portions, such as their ends, secured in one or more of such fused areas 42, such that the fused areas are primarily involved in anchoring the loop fibers against pullout from hook loads. Whether the welds are discrete points or an interconnected grid, this further secures the fibers, helping to strengthen the loop structures 48. The laminating occurs while the loop structures 48 are safely disposed between pins 102, such that no pressure is applied to crush the loops during bonding. Protecting the loop structures during lamination significantly improves the performance of the material as a touch fastener, as the loop structures remain extended from the base for hook engagement.

If desired, a backing sheet (not shown) can be introduced between the hot can and the needled web, such that the backing sheet is laminated over the back surface of the loop product while the fibers are bonded under pressure from the pins of apron 22.

Referring back to FIG. 1, from lamination station 92 the laminated web moves through another accumulator 90 to an embossing station 104, where a desired pattern of locally raised regions is embossed into the web between two counter-rotating embossing rolls. In some cases, the web may move directly from the laminator to the embossing station, without accumulation, so as to take advantage of any latent temperature increase caused by lamination. The loop side of the bonded loop product is embossed with a desired embossing pattern prior to spooling. In this example the loop product is passed through a nip between a driven embossing roll 54 and a backup roll 56. The embossing roll 54 has a pattern of raised areas that permanently crush the loop formations against the carrier sheet, and may even melt a proportion of the fibers in those areas. Embossing may be employed simply to enhance the texture or aesthetic appeal of the final product. In some cases, roll 56 has a pattern of raised areas that mesh with dimples in roll 54, such that embossing results in a pattern of raised hills or convex regions on the loop side, with corresponding concave regions on the non-working side of the product, such that the embossed product has a greater effective thickness than the pre-embossed product. Additionally, embossing presents the loop structures 48 or otherwise engageable fiber portions at different angles to a mating field of hooks, for better engagement.

The embossed web then moves through a third accumulator 90, past a metal detector 106 that checks for any broken needles or other metal debris, and then is slit and spooled for storage or shipment. During slitting, edges may be trimmed and removed, as can any undesired carrier sheet overlap region necessitated by using multiple parallel strips of carrier sheet.

We have found that, using the process described above, a useful loop product may be formed with relatively little fiber 12. In one example, mat 10 has a basis weight of only about 1.0 osy (33 grams per square meter). Fibers 12 are drawn and crimped polyester fibers, 3 to 6 denier, of about a four-inch (10 centimeters) staple length, mixed with crimped bicomponent polyester fibers of 4 denier and about two-inch (5 centimeters) staple length. The ratio of fibers may be, for example, 80 percent solid polyester fiber to 20 percent bicomponent fiber. In other embodiments, the fibers may include 15 to 30 percent bicomponent fibers. The preferred ratio will depend on the composition of the fibers and the processing conditions. Generally, too little bicomponent fiber may compromise loop anchoring, due to insufficient fusing of the fibers, while too much bicomponent fiber will tend to increase cost and may result in a stiff product and/or one in which some of the loops are adhered to each other. The bicomponent fibers are core/sheath drawn fibers consisting of a polyester core and a copolyester sheath having a softening temperature of about 110 degrees Celsius, and are employed to bind the solid polyester fibers to each other and the carrier.

In this example, both types of fibers are of round cross-section and are crimped at about 7.5 crimps per inch (3 crimps per centimeter). Suitable polyester fibers are available from INVISTA of Wichita, Kans., (www.invista.com) under the designation Type 291. Suitable bicomponent fibers are available from INVISTA under the designation Type 254. As an alternative to round cross-section fibers, fibers of other cross-sections having angular surface aspects, e.g. fibers of pentagon or pentalobal cross-section, can enhance knot formation during needling.

Loop fibers with tenacity values of at least 2.8 grams per denier have been found to provide good closure performance, and fibers with a tenacity of at least 5 or more grams per denier (preferably even 8 or more grams per denier) are even more preferred in many instances. In general terms for a loop-limited closure, the higher the loop tenacity, the stronger the closure. The polyester fibers of mat 10 are in a drawn, molecular oriented state, having been drawn with a draw ratio of at least 2:1 (i.e., to at least twice their original length) under cooling conditions that enable molecular orientation to occur, to provide a fiber tenacity of about 4.8 grams per denier.

The loop fiber denier should be chosen with the hook size in mind, with lower denier fibers typically selected for use with smaller hooks. For low-cycle applications for use with larger hooks (and therefore preferably larger diameter loop fibers), fibers of lower tenacity or larger diameter may be employed.

For many applications, particularly products where the hook and loop components will be engaged and disengaged more than once ("cycled"), it is desirable that the loops have relatively high strength so that they do not break or tear when the fastener product is disengaged. Loop breakage causes the loop material to have a "fuzzy," damaged appearance, and widespread breakage can deleteriously effect re-engagement of the fastener.

Loop strength is directly proportional to fiber strength, which is the product of tenacity and denier. Fibers having a fiber strength of at least 6 grams, for example at least 10 grams, provide sufficient loop strength for many applications. Where higher loop strength is required, the fiber strength may be higher, e.g., at least 15. Strengths in these ranges may be obtained by using fibers having a tenacity of about 2 to 7 grams/denier and a denier of about 1.5 to 5, e.g., 2 to 4. For example, a fiber having a tenacity of about 4 grams/denier and a denier of about 3 will have a fiber strength of about 12 grams.

Other factors that affect engagement strength and cycling are the geometry of the loop structures, the resistance of the loop structures to pull-out, and the density and uniformity of the loop structures over the surface area of the loop product. The first two of these factors are discussed above. The density and uniformity of the loop structures is determined in part by the coverage of the fibers on the carrier sheet. In other words, the coverage will affect how many of the needle penetrations will result in hook-engageable loop structures. Fiber coverage is indicative of the length of fiber per unit area of the carrier sheet, and is calculated as follows:

Fiber coverage (meters per square meter)=Basis Weight/Denier×9000

Thus, in order to obtain a relatively high fiber coverage at a low basis weight, e.g., less than 2 osy, it is desirable to use relatively low denier (i.e., fine) fibers. However, the use of low denier fibers will require that the fibers have a higher tenacity to obtain a given fiber strength, as discussed above. Higher tenacity fibers are generally more expensive than lower tenacity fibers, so the desired strength, cost and weight characteristics of the product must be balanced to determine the appropriate basis weight, fiber tenacity and denier for a particular application. It is generally preferred that the fiber layer of the loop product have a calculated fiber coverage of at least 50,000, preferably at least 90,000, and more preferably at least 100,000.

To produce loop materials having a good balance of low cost, light weight and good performance, it is generally preferred that the basis weight be less than 2.0 osy, e.g., 1.0 to 2.0 osy, and the coverage be about 50,000 to 200,000.

Various synthetic or natural fibers may be employed. In some applications, wool and cotton may provide sufficient fiber strength. Presently, thermoplastic staple fibers which have substantial tenacity are preferred for making thin, low-cost loop product that has good closure performance when paired with very small molded hooks. For example, polyolefins (e.g., polypropylene or polyethylene), polyesters (e.g., polyethylene terephthalate), polyamides (e.g., nylon), acrylics and mixtures, alloys, copolymers and co-extrusions thereof are suitable. Polyester is presently preferred. Fibers having high tenacity and high melt temperature may be mixed with fibers of a lower melt temperature resin. For a product having some electrical conductivity, a small percentage of metal fibers may be added. For instance, loop products of up to about 5 to 10 percent fine metal fiber, for example, may be advantageously employed for grounding or other electrical applications.

In one example, mat 10 is laid upon a blown polyethylene film 14, such as is available for bag-making and other packaging applications. Film 14 has a thickness of about 0.002 inch (0.05 millimeter). Even thinner films may be employed, with good results. Other suitable films include polyesters, polypropylenes, EVA, and their copolymers. Other carrier web materials may be substituted for film 14 for particular applications. For example, fibers may be needle-punched into paper, scrim, or fabrics such as non-woven, woven or knit materials, for example lightweight cotton sheets. If paper is used, it may be pre-pasted with an adhesive on the fiber side to help bond the fibers and/or a backing layer to the paper.

Still referring to FIG. 1, in some cases a wire screen is used in place of both the bed of pins or bristles 20 and driven support belt 22, for an analogous needling process. The wires define openings through which the needle passes as it draws fibers 12 through the carrier sheet 14. Suitable screens can be made from materials including bronze, copper, brass, and stainless steel. We have found that screens made of brass wire with a nominal diameter of between about 0.02 and 0.03 inch (0.5 and 0.8 millimeter) or, more preferably, between about 0.023 and 0.028 inch (0.6 and 0.7 millimeter), are resilient without being too stiff. Screens having openings with a nominal width of between about 0.05 and 0.2 inch (1.3 and 5.1 millimeter) or, more preferably, between about 0.06 and 0.1 inch (1.5 and 2.5 millimeter) are appropriate for this purpose. Such screens are available from McMaster-Carr Supply Co. of Elmhurst, Ill. under the designation 9223T41.

Figure 4:
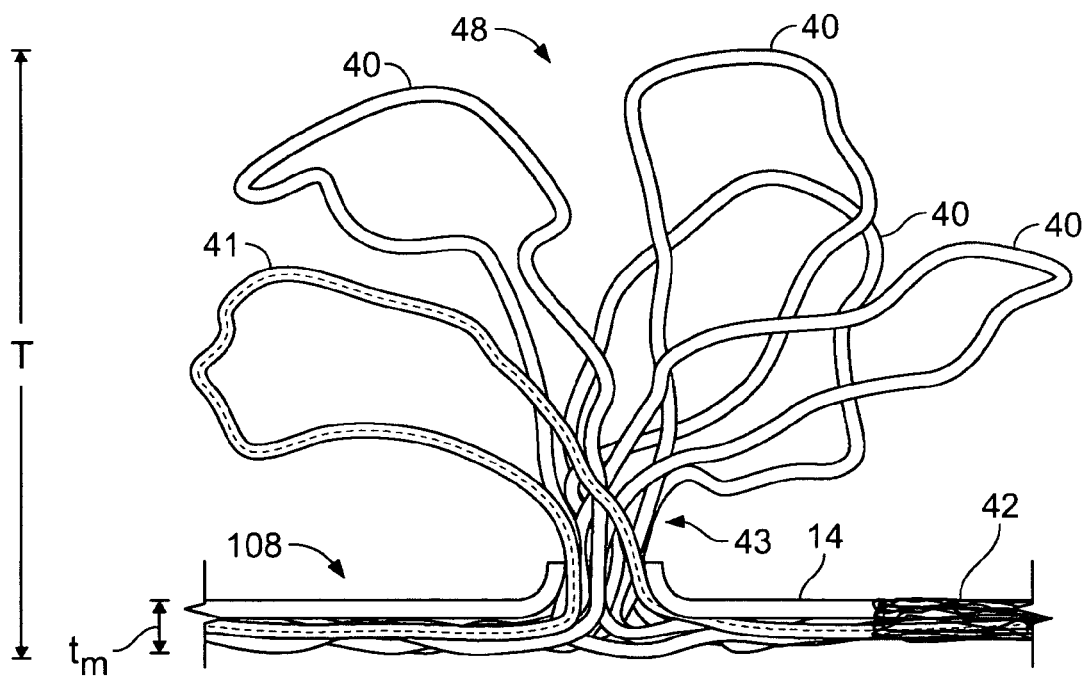
FIG. 4 is a highly enlarged diagrammatic view of a loop structure formed by needling with fork needles through film.

FIG. 4 is an enlarged view of a loop structure 48 containing multiple loops 40 extending from a common trunk 43 through a hole in film 14, as formed by the above-described method. As shown, loops 40 stand proud of the underlying film, available for engagement with a mating hook product, due at least in part to the vertical stiffness of trunk 43 of each formation, which is provided both by the constriction of the film material about the hole and the anchoring of the fibers to each other and the film. This vertical stiffness acts to resist permanent crushing or flattening of the loop structures, which can occur when the loop material is spooled or when the finished product to which the loop material is later joined is compressed for packaging. Resiliency of the trunk 43, especially at its juncture with the base, enables structures 48 that have been "toppled" by heavy crush loads to right themselves when the load is removed. The various loops 40 of formation 48 extend to different heights from the film, which is also believed to promote fastener performance. Because each formation 48 is formed at a site of a penetration of film 14 during needling, the density and location of the individual structures are very controllable. Preferably, there is sufficient distance between adjacent structures so as to enable good penetration of the field of formations by a field of mating male fastener elements (not shown). Each of the loops 40 is of a staple fiber whose ends are disposed on the opposite side of the carrier sheet, such that the loops are each structurally capable of hook engagement. One of the loops 40 in this view is shown as being of a bicomponent fiber 41. The material of the high-tenacity fibers may be selected to be of a resin with a higher melt temperature than the film. After laminating, the film and fibers become permanently bonded together at discrete points 42 corresponding to the distal ends of pins 20.

Because of the relatively low amount of fibers remaining in the mat, together with the thinness of the carrier sheet and any applied backing layer, mat 108 can have a thickness "$t_m$" of only about 0.008 inch (0.2 millimeters) or less, preferably less than about 0.005 inch, and even as low as about 0.001 inch (0.025 millimeter) in some cases. The carrier film 14 has a thickness of less than about 0.002 inch (0.05 millimeter), preferably less than about 0.001 inch (0.025 millimeter) and even more preferably about 0.0005 inch (0.013 millimeter). The finished loop product 30 has an overall thickness "T" of less than about 0.15 inch (3.7 millimeters), preferably less than about 0.1 inch (2.5 millimeters), and in some cases less than about 0.05 inch (1.3 millimeter). The overall weight of the loop fastener product, including carrier sheet, fibers and fused binder (an optional component, discussed below), is preferably less than about 5 ounces per square yard (167 grams per square meter). For some applications, the overall weight is less than about 2 ounces per square yard (67 grams per square meter), or in one example, about 1.35 ounces per square yard (46 grams per square meter).

Figure 4A:
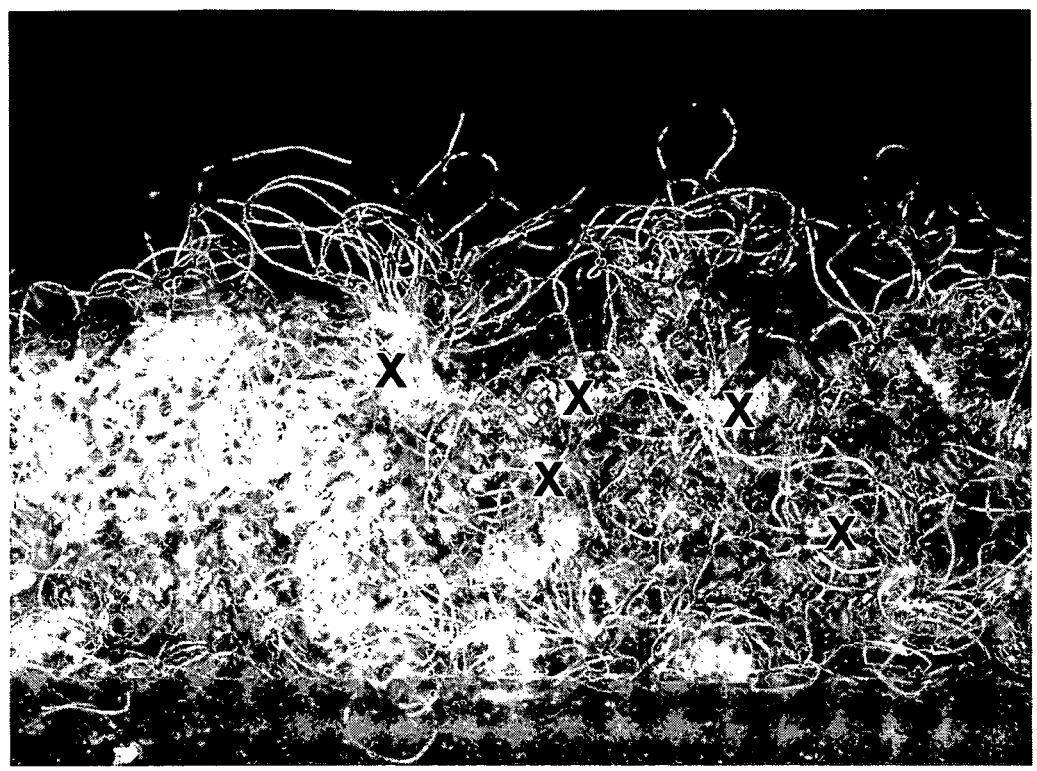
FIG. 4A is an enlarged photograph of a rolled edge of a loop product formed by needling with fork needles through film, showing several discrete loop structures.
Figure 4B:
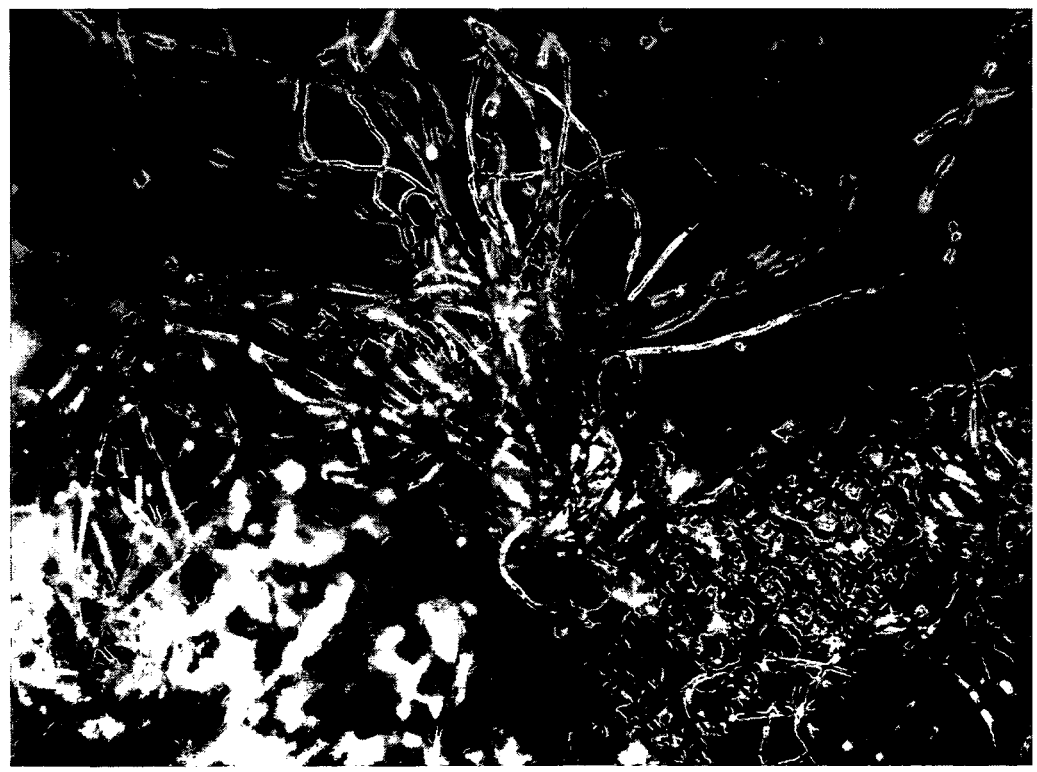
FIG. 4B is a highly enlarged photograph of one of the loop structures shown in FIG. 4A.

FIG. 4A is an enlarged photograph of a loop product formed by needling fibers through a film with fork needles. The view is taken toward a folded edge of the product, so as to spread out the loop structures for increased visibility. Five of the loop structures shown in the photograph have been marked with an 'X'. The surface of the film is clearly visible between the loop structures, each of which contains many individual loops emanating from a common trunk, as shown in FIG. 4B, an enlarged view of a single one of the loop structures. In FIG. 4B, light is clearly seen reflected at the base of the loop structure from film that has been raised about the hole during piercing, and that subsequently bears against the loop fibers in the hole, stiffening the trunk of the loop structure. An outline of the raised portion of film is shown on the photograph.

Figure 4C:
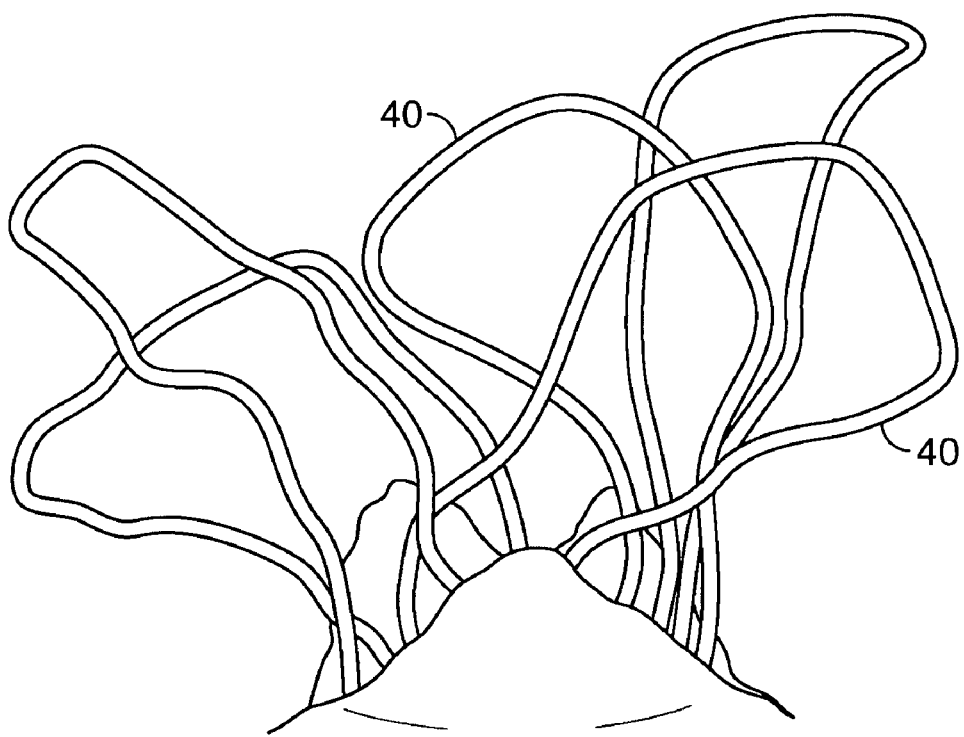
FIG. 4C illustrates a loop structure formed by needling with crown needles through polyester film.

Fork needles tend to produce the single-trunk structures as shown in FIG. 4, which we call 'loop trees.' Crown needles, by contrast, tend to create more of a 'loop bush' structure, as illustrated in FIG. 4C, particularly in film carrier sheets. As the barbs of crown needles go through the film, they are more likely to tear the film, perhaps due to increased notch sensitivity. In polyester films, such crown needle film fracturing limits the practical maximum punch density. We have not seen such fracturing in polyethylene, but did observe barb notching. In either case, the film hole created by a crown needle doesn't tend to create the 'turtleneck' effect as in FIG. 4, with the result that the fibers passing through the film are not as securely supported. Well-supported loop trees are more able to resist crushing, such as from spooling of the loop material, than less-supported bush structures. Fork needles also tend to create a field of loop structures of more uniform height, whereas felting needles with multiple barb heights tend to create loop structures of more varying loop height. Furthermore, as fork needles wear, they tend to carry more, rather than fewer, loops. Teardrop needles may also be employed, and may reduce the tendency to tear off small 'chads' of film that can be formed by fork needles.

Figure 5:
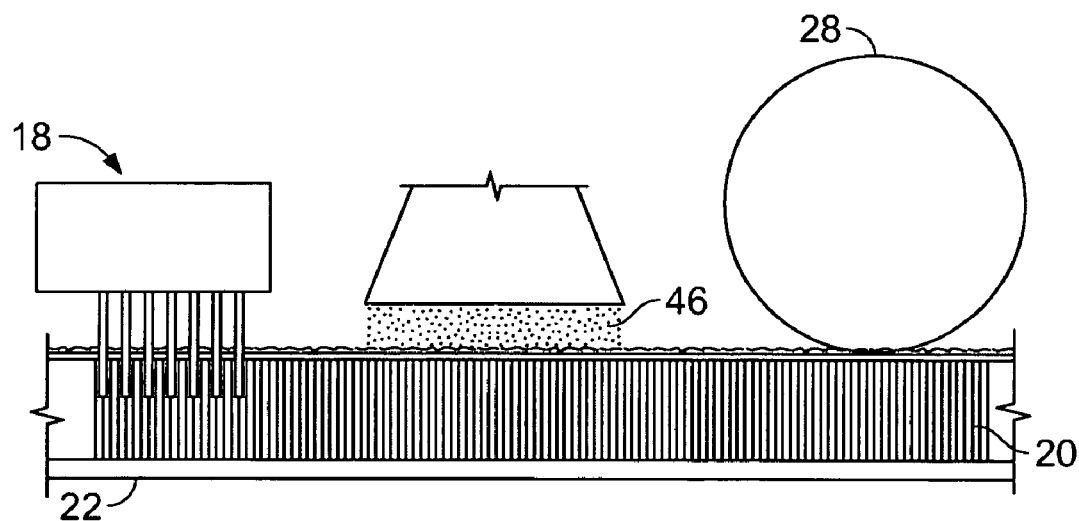
FIG. 5 is a diagrammatic view showing an alternative lamination step utilizing a powder-form binder.

Referring next to FIG. 5, in an alternative lamination step a powdered binder 46 is deposited over the fiber side of the needle-punched film and then fused to the film by roll 28 or a flatbed laminator. For example, a polyethylene powder with a nominal particle size of about 20 microns can be sprinkled over the fiber-layered polyethylene film in a distribution of only about 0.5 ounces per square yard (17 grams per square meter). Such powder is available in either a ground, irregular shape or a generally spherical form from Equistar Chemicals LP in Houston, Tex. Preferably, the powder form and particle size are selected to enable the powder to sift into interstices between the fibers and contact the underlying film. It is also preferable, for many applications, that the powder be of a material with a lower melt temperature than the loop fibers, such that during bonding the fibers remain generally intact and the powder binder fuses to either the fibers or the carrier web. In either case, the powder acts to mechanically bind the fibers to the film in the vicinity of the supporting pins and anchor the loop structures. In sufficient quantity, powder 46 can also form at least a partial backing in the finished loop product, for permanently bonding the loop material onto a compatible substrate. Other powder materials, such as polypropylene or an EVA resin, may also be employed for this purpose, with appropriate carrier web materials, as can mixtures of different powders.

Figure 6:
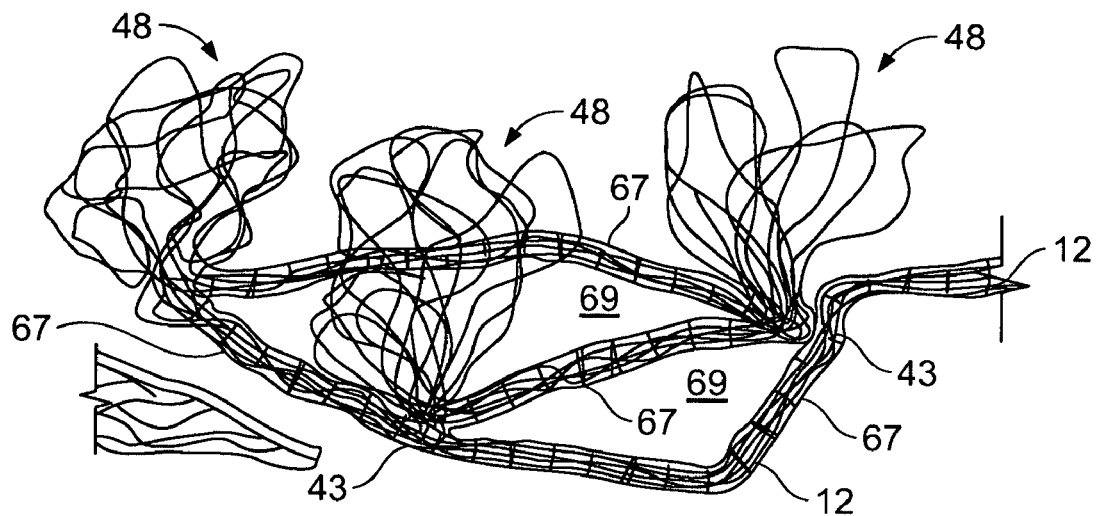
FIG. 6 is a highly enlarged diagrammatic view of a loop material according to an embodiment in which the carrier film is substantially disintegrated during needling.
Figure 7B:
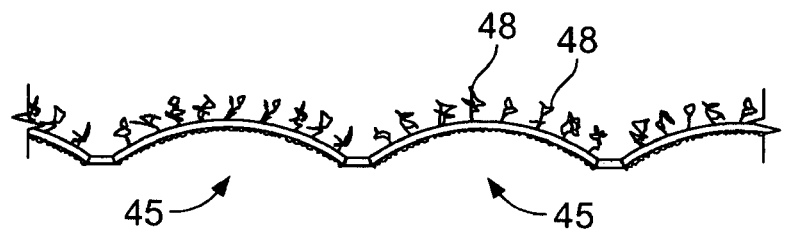
FIG. 7B is a highly enlarged diagrammatic view of an embossed loop material having convex regions.

Referring back to FIG. 1, in some cases the needling parameters (e.g., needle size, needling density) can be selected to cause the carrier web 14 to be practically disintegrated during needling. While this is undesirable for some applications, we have found that such a structure is advantageous for other uses. For example, in one case a fiber-covered 0.002 inch (0.05 millimeter) polyethylene film was needled with 30 gauge forked needles to a penetration density of 250 penetrations per square centimeter, resulting in a structure as shown in FIG. 6, in which the fibers 12 themselves formed practically the only connectivity within the needled sheet. The film itself remained in the form of discrete portions 69 separated by cracks 67 extending between adjacent loop trunks 43. This structure was sufficiently dimensionally stable to be laminated to a stretchable backing film, such as a polypropylene or polyethylene film available from Tredegar Film Products in Richmond, Va. During lamination, the discrete segments 66 of carrier film bonded to the stretchable backing, further anchoring the bases of the loop structures while permitting the final loop product to be elastically stretchable within its plane.

A pre-printed film or paper may be employed as the carrier web to provide graphic images visible from the loop side of the finished product. The small bonding spots and the low density of fiber remaining in the mat generally do not significantly detract from the visibility of the image. This can be advantageous, for example, for loop materials to be used on children's products, such as disposable diapers. In such cases, child-friendly graphic images can be provided on the loop material that is permanently bonded across the front of the diaper chassis to form an engagement zone for the diaper tabs. The image can be pre-printed on either surface of an otherwise transparent carrier film.

A finished loop product may be embossed with a honeycomb pattern. Graphic images printed on the back side of the carrier film (opposite the loop side) may in some cases be clearly visible through the loops. Printing on the back side of the film causes the ink to be encapsulated by fibers remaining on the back side of the film, to avoid ink wear. Various other embossing patterns include, as examples, a grid of intersecting lines forming squares or diamonds, or a pattern that crushes the loop formations other than in discrete regions of a desired shape, such as round pads of loops. The embossing pattern may also crush the loops to form a desired image, or text, on the loop material. In some cases, each cell of the embossing pattern may be a closed hexagon containing multiple discrete loop structures. The width 'W' between opposite sides of the open area of each cell may be about 6.5 millimeters, while the thickness 't' of the wall of the cell may be about 0.8 millimeter.

Figure 8:
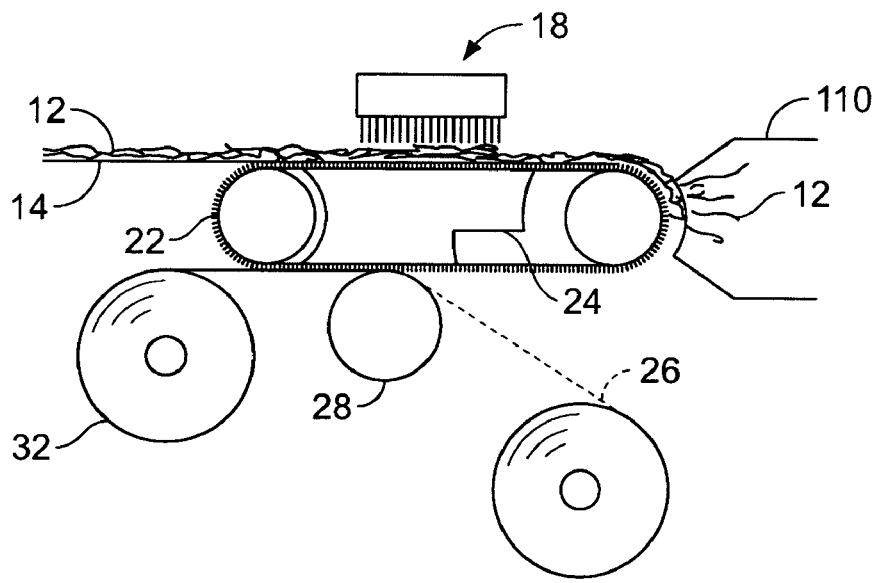
FIG. 8 is a diagrammatic view of a process for forming a loop material having discrete regions of loop while removing non-needled fibers from the carrier web.

Referring to FIG. 8, in one method of forming a product with only discrete regions of loop the fiber-covered carrier web is needled only in desired regions, leaving other areas of the web unpenetrated. The fibers in the non-needled regions remain generally loose and are readily removed from the carrier web, such as by vacuum 110. Removed fibers are readily re-carded and thus recycled. The needled web is then optionally laminated to a backing 26, fusing to the carrier sheet in the fiber-covered and needled regions as well as in the fiber-free regions. Alternatively, the fibers are fused to each other and/or the carrier sheet under pressure applied by hot can 28, without an added backing layer. The laminate product is then spooled for later use.

Figure 9:
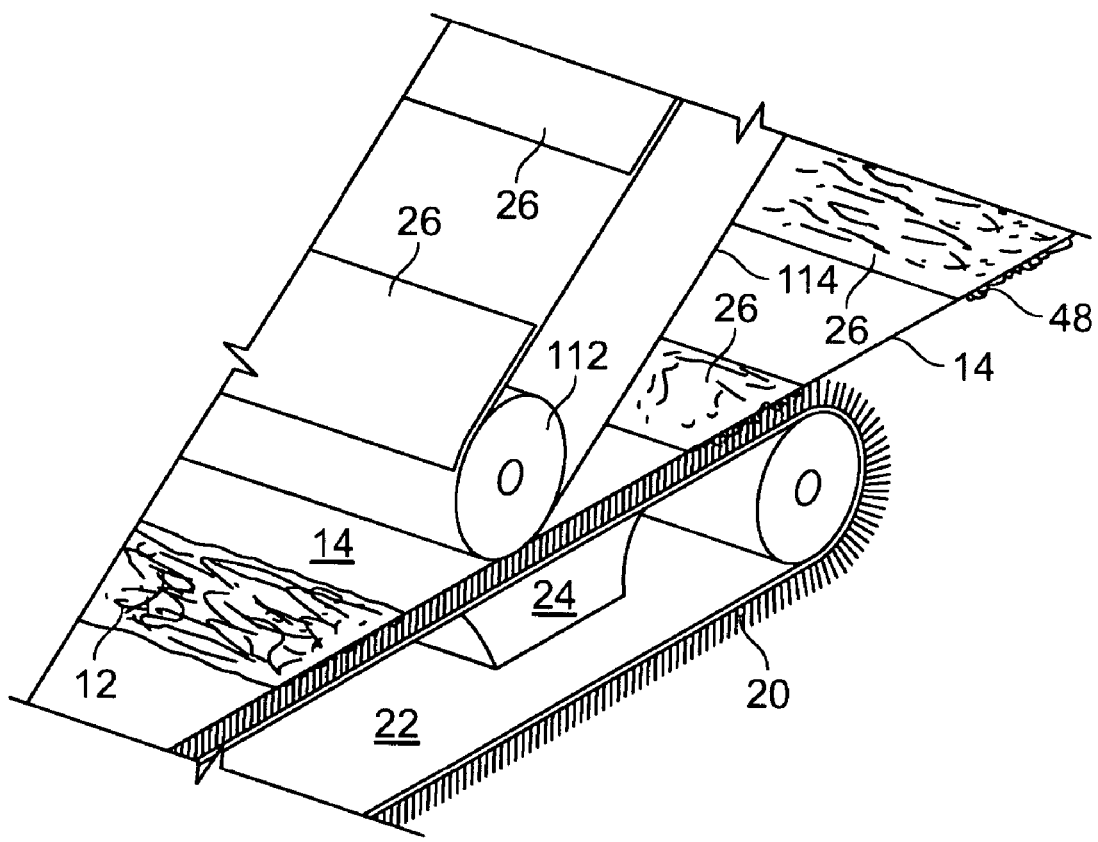
FIG. 9 is a diagrammatic view of a process for rendering needled portions of a loop product substantially fluid-impermeable.

In the alternative bonding process illustrated in FIG. 9, discrete patches of backing 26 are applied to cover the needled and fiber-bearing regions of carrier web 14, leaving the remaining regions of the carrier web uncovered and unlaminated. Each backing patch 26 is bonded in place by pressure from roller 112 to cover the fibers remaining on the back surface of the carrier web. Fluid impermeable patches 26 can be employed to seal the needled holes, thereby creating a fluid-impermeable finished product of particularly low weight and nominal thickness. In some cases, backing patches 26 are pre-coated with an adhesive that adheres the backing to the film and bonds the fibers. Patches 26 can be delivered to carrier 14 on a circulating conveyor belt 114 in a labeling process, as shown.

If the needled regions of the loop product are covered with a backing material 26 selected to be liquid impermeable, then the entire loop product can be formed to provide a barrier to liquids. If fibers 12 are selected to be absorbent, such as of cotton or cellulosic acetate, then the final loop product can be employed to wick liquids into the mat via the exposed loops 40.

Referring back to FIG. 1, another method of forming a product with only discrete regions of loop involves depositing staple fibers onto the carrier sheet 14 only in desired regions, leaving other regions of the carrier generally void of fibers, and then needling, laminating and embossing the sheet as described above, without regard to where the fibers are disposed. In this manner, loose fibers need not be removed from the product after needling. Discrete doses of fiber can be deposited onto the carrier through a template or screen, for example. Alternatively, the second carding doffer can be configured to supply discrete amounts of fibers to the condenser, or a light adhesive may be pre-applied to the carrier sheet only where fibers are desired, and then fibers applied over the extent of the film and removed where not lightly bonded.

The above-described processes enable the cost-effective production of high volumes of loop materials with good fastening characteristics. They can also be employed to produce loop materials in which the materials of the loops, substrate and optional backing are individually selected for optimal qualities. For example, the loop fiber material can be selected to have high tenacity for fastening strength, while the substrate and/or backing material can be selected to be readily bonded to other materials without harming the loop fibers.

The materials of the loop product can also be selected for other desired properties. In one case the loop fibers, carrier web and backing are all formed of polypropylene, making the finished loop product readily recyclable. In another example, the loop fibers, carrier web and backing are all of a biodegradable material, such that the finished loop product is more environmentally friendly. High tenacity fibers of biodegradable polylactic acid are available, for example, from Cargill Dow LLC under the trade name NATUREWORKS. In another example, carbon fibers are needle-punched into a KEVLAR film and bonded with silicone or other high temperature adhesive to produce a loop material with excellent fire resistance.

Polymer backing layers or binders may be selected from among suitable polyethylenes, polyesters, EVA, polypropylenes, and their co-polymers. Paper, fabric or even metal may be used. The binder may be applied in liquid or powder form, and may even be pre-coated on the fiber side of the carrier web before the fibers are applied. In many cases, a separate binder or backing layer is not required, such as for low cycle applications in disposable personal care products, such as diapers.

In one test, 3 denier crimped polyester fibers were carded and laid over an 0.002 inch (0.05 millimeter) thick sheet of blown polyethylene film in a layer having a basis weight of about 1.0 ounce per square yard (33 grams per square meter). The fiber-covered film was then needled with 38 gauge tufting needles, from the fiber side, at a needling density of 250 punches per square centimeter, and a penetration depth of 3.3 millimeters. The back of the needled material was bonded to a 0.001 inch (0.025 millimeter) thick sheet of polyethylene against a bed of pins. Mated with a molded hook product with CFM-29 hooks in a density of about 264 hooks per square centimeter from Velcro USA in Manchester, N.H., the loops achieved an average peel of about 500 grams per inch (200 grams per centimeter), as tested according to ASTM D 5170-91. Mated with this same hook product, the loop material achieved an average shear of about 7,000 grams per square inch (1100 grams per square centimeter), as tested according to ASTM D 5169-91. Tested against a CFM-85 palm tree hook from Velcro USA, the loop material achieved roughly 600 grams per inch (240 grams per centimeter) of peel and 6,000 grams per square inch (930 grams per square centimeter) of shear.

In another example, a loop product was prepared as in the test just described, except that the fibers were 6 denier, the needling density was 225 punches per square centimeter, and the needling depth was 4.4 centimeters. This loop material achieved roughly 550 grams per inch (215 grams per centimeter) of peel and 5,000 grams per square inch (775 grams per square centimeter) of shear against the CFM-29 hook product, and roughly 270 grams per inch (105 grams per centimeter) of peel and 5,500 grams per square inch (850 grams per square centimeter) of shear against the CFM-85 hook product.

In another test, the blend of 80 percent 3 denier crimped polyester fibers and 20 percent 4 denier bicomponent polyester fibers described above were carded and laid over an 0.0005 inch (0.013 millimeter) thick sheet of cast polypropylene film in a layer having a basis weight of about 1.0 ounce per square yard (34 grams per square meter). The fiber-covered film was then needled with 38 gauge fork needles, from the fiber side, at a needling density of 80 punches per square centimeter, and a penetration depth of 5.0 millimeters. The needled material was laminated with the lamination method described above with reference to FIG. 1. Mated with a molded hook product with CFM-69 hooks from Velcro USA, with a hook density of about 1,300 per square inch (200 hooks per square centimeter), the loops achieved an average peel of about 380 grams per inch (150 grams per centimeter), as tested according to ASTM D 5170-91. Mated with this same hook product, the loop material achieved an average shear of about 3,800 grams per square inch (600 grams per square centimeter), as tested according to ASTM D 5169-91. Mated with a molded hook product with CFM-108 hooks from Velcro USA (under part designation HTH 847), with a hook density of about 1,300 per square inch (200 hooks per square centimeter), the loops achieved an average peel of about 300 grams per inch (120 grams per centimeter), as tested according to ASTM D 5170-91. Mated with this same hook product, the loop material achieved an average shear of about 3,000 grams per square inch (475 grams per square centimeter), as tested according to ASTM D 5169-91.

A number of embodiments of the invention have been described. Nevertheless, it will be understood that various modifications may be made without departing from the spirit and scope of the invention. Accordingly, other embodiments are within the scope of the following claims.

What is claimed is:

1. A method of forming a loop product, the method comprising
   introducing a sheet-form substrate and a layer of polymeric fibers into a needle loom, with the fibers disposed on a first surface of the substrate; and
   needling the fibers through the substrate to form hook-engageable loop structures of the fibers extending from a second surface of the substrate through holes formed in the substrate by the needling,
   wherein needling the fibers includes
      piercing the substrate with a plurality of needles while advancing the substrate in a machine direction at a predetermined speed, the needles being configured to form the hook-engageable loop structures, while
      cyclically advancing the needles in the machine direction, during piercing of the substrate, in a manner that causes the needles to travel in a substantially elliptical path, such that while the needles extend through the substrate the needles are moving in the machine direction.

2. The method of claim 1 further comprising, after needling, anchoring the loop structures to resist fiber pullout under fastening loads.

3. The method of claim 2 further comprising embossing the loop product after anchoring the loop structures.

4. The method of claim 2 wherein anchoring includes laminating fiber portions to the first surface of the substrate.

5. The method of claim 4 wherein laminating includes passing the needled substrate through a nip between two rolls, one of the two rolls having a plurality of pins extending from its surface.

6. The method of claim 5 further comprising preheating the needled substrate prior to delivering it to the nip.

7. The method of claim 4 wherein laminating is performed in a manner so as to avoid crushing the loop structures.

8. The method of claim 2 wherein the fibers comprise bicomponent fibers that include an inner layer and an outer layer, the outer layer having a lower softening temperature than the inner layer.

9. The method of claim 8 wherein anchoring comprises heating the needled substrate sufficiently to soften the outer layer of the bicomponent fibers and fuse fiber portions to the first surface of the substrate.

10. The method of claim 8 wherein the bicomponent fibers comprise core-sheath fibers wherein the sheath has a lower melting point than the core.

11. The method of claim 10 wherein the core is a polyester and the sheath is a copolyester.

12. The method of claim 8 wherein the fibers comprise a blend of bicomponent fibers and single component fibers.

13. The method of claim 12 wherein the blend includes between about 15 and 30 percent bicomponent fibers, by weight.

14. The method of claim 1 wherein the needling step further comprises providing a bed of brushes or lamella into which the needles penetrate after piercing the substrate.

15. The method of claim 14 wherein the needling step comprises a random velouring process.

16. The method of claim 1 wherein the predetermined speed of the substrate is at least 30 meters per minute.

17. The method of claim 1 wherein the holes arc substantially round.

18. The method of claim 1 wherein the holes are oval and have a length, in the machine direction, which is less than 20 percent greater than their width in a cross-machine direction.

19. The method of claim 1 wherein the substrate comprises a polymer film.

20. The method of claim 1 wherein the substrate comprises a scrim.

21. The method of claim 1 wherein the substrate comprises paper.

22. The method of claim 1 wherein the needling step comprises elliptical needling.

23. The method of claim 1 wherein the needling step comprises needling into a moving support.

24. The method of claim 23 wherein the moving Support comprises a brush apron.

25. A method of forming a loop product, the method comprising
- introducing a sheet-form substrate and a layer of polymeric fibers into a needle loom, with the fibers disposed on a first surface of the substrate;
- supporting the substrate on a support selected from the group consisting of a bristle bed, a flat lammela bed, or a stack of lammela disks; and
- needling the fibers through the substrate into the support from only one direction, using a random velouring process, to form hook-engageable loop structures of the fibers extending from a second surface of the substrate through holes formed in the substrate by the needling, wherein needling the fibers includes
- piercing the substrate with a plurality of needles configured to form the hook-engageable loop structures while advancing the substrate in a machine direction at a predetermined speed, while
- cyclically advancing the needles in the machine direction, during piercing of the substrate, in a manner that causes the needles to travel in a substantially elliptical path, such that while the needles extend through the substrate the needles are moving in the machine direction.

* * * * *

UNITED STATES PATENT AND TRADEMARK OFFICE
CERTIFICATE OF CORRECTION

PATENT NO. : 7,562,426 B2
APPLICATION NO. : 11/102606
DATED : July 21, 2009
INVENTOR(S) : James R. Barker Page 1 of 1

It is certified that error appears in the above-identified patent and that said Letters Patent is hereby corrected as shown below:

On the Title Page, Item (75) (Inventors), delete "Francistown" and insert --Francestown--;

Column 17, line 11 (Claim 17), delete "arc" and insert --are--;

Column 17, line 26 (Claim 24), delete "Support" and insert --support--.

Signed and Sealed this

Twenty-ninth Day of September, 2009

David J. Kappos
*Director of the United States Patent and Trademark Office*